United States Patent [19]
Gömöri

[11] Patent Number: 4,915,955
[45] Date of Patent: Apr. 10, 1990

[54] PROCESS FOR PREPARING A DISINFECTANT

[75] Inventor: Janos Gömöri, Stäfa, Switzerland

[73] Assignee: Sanosil AG., Feldmeilen, Switzerland

[21] Appl. No.: 904,055

[22] Filed: Sep. 5, 1986

[30] Foreign Application Priority Data

Apr. 22, 1986 [CH] Switzerland .................. 1629/86

[51] Int. Cl.$^4$ ................. A01N 39/00; A01N 59/16
[52] U.S. Cl. ................................ 424/616; 424/618
[58] Field of Search ............. 424/132, 128, 130, 616, 424/618; 514/495

[56] References Cited

U.S. PATENT DOCUMENTS 3,422,183  1/1969  Ellison ............................ 424/132
4,595,591  6/1986  Mardi et al. ..................... 424/132

FOREIGN PATENT DOCUMENTS 2302277  2/1976  Netherlands.

OTHER PUBLICATIONS

Abstract—English-Language Equivalent of DE 2302277, "Stable High Solids Silver Soln. Prepn.—for Use E.G. in Preventing Algae Growth in Swimming Pools, by Redn. of Silver Salts in Presence of Polyaldehyde Acids/Salts".
Degussa pamphlet entitled "POC," pp. 1–25.
SANOSIL® Product Brochure, Sanosil, Ltd., CH-8705 Feldmeilen, Switzerland, pp. 1–17.

*Primary Examiner*—Douglas W. Robinson
*Assistant Examiner*—Kevin E. Weddington
*Attorney, Agent, or Firm*—Webb, Burden, Ziesenheim & Webb

[57] ABSTRACT

A concentrate with an unlimited shelf-life, which can be mixed with hydrogen peroxide at a ratio of 1:99 to 1:199 to become an effective disinfectant, is obtained when a viscous solution of inorganic acid, with a pH less than or equal to 1.6, is mixed with a silver salt compound or a colloidal silver compound at 50° to 60° C. The mixture is further combined at room temperature with other inorganic acid(s) to reach a total of 100 g inorganic acid(s) per liter of water; at room temperature, an organic acid stabilizer is added and the mixture is homogenized. The concentrate, during storage, remains homogeneous and crystal-clear.

12 Claims, No Drawings

PROCESS FOR PREPARING A DISINFECTANT

FIELD OF THE INVENTION

The present invention relates to a process for the manufacture of a concentrate which can be mixed with hydrogen peroxide to form a disinfectant.

INTRODUCTION

Disinfection, especially of water, foodstuffs and animal feeds as well as equipment, packages, containers and objects of all kinds, is a worldwide problem of importance in highly civilized nations and underdeveloped countries alike. It is therefore not surprising that intensive research has been ongoing in this area for decades, and that new products and methods for the non-therapeutic battle against infectious agents are constantly being developed.

Of the numerous known prior art disinfection methods, the following are exemplary.

The addition of halogens such as chlorine, bromine and iodine, or of halogen-releasing compositions, is popular due to the ease of manufacture, low price, and ready availability of the constituent chemicals, as well as for its reliable germicidal action. Disadvantages include the initial taste and odor of the halogen, the change in taste of the compositions mixed with it, the overall basic pH, the relatively short duration of the germicidal activity, and the concomitant temperature sensitivity of the resultant combinations. In addition, these substances are carcinogenic and mutagenic, cause skin irritations, and are corrosive to a variety of materials.

Ozone and chlorine dioxide combine to form an especially quick and effective disinfectant, but the resultant combination remains effective for only a short time. These combined agents can also be very dangerous in large doses. Furthermore, they display temperature sensitivity, tend to be carcinogenic and mutagenic, and require both careful handling and expensive auxiliary equipment. They are therefore suitable only for a very narrow area of application.

Copper salts, especially copper sulfate and copper chloride, are recommended as disinfectants that are odorless and which do not irritate mucous membranes, etc. These combinations, which produce only an average, briefly-sustained disinfecting rate and are known to be carcinogenic and mutagenic, especially the chloride salts, do combine readily with other substances.

Processes which are common, odorless, and have no adverse effects on health are the so-called Catadyne method and similar methods utilizing the germicidal effect of silver ions. This process is slow-working and has limited application due to its high cost.

Ultraviolet radiation, which does not introduce foreign matter into the substance to be disinfected, is a reliable source of germicide activity. The generation of ultraviolet radiation, however, requires both expensive equipment and the substantial costs commensurate with large electricity requirements.

Other commercially available products rely heavily on the powerful germicidal activity of hydrogen peroxide, but such compositions have limited utility due to their instability. These compositions include those which combine the well-known germicidal effects of silver with hydrogen peroxide, in the form of a stable agent, to cause a synergy of the two disinfecting agents.

As a result of the present invention, it is now possible to make products of this last type, having substantially improved quality and utility, by means of a new process.

It is an object of the present invention to provide a method for manufacturing a clear, stable concentrate which can be mixed with hydrogen peroxide to form a disinfectant, and which contains silver, an inorganic acid and an organic stabilizer.

It is a further object of the present invention to provide a concentrate of that type as well as a process for the manufacture of a disinfectant from such a concentrate.

SUMMARY OF THE INVENTION

The present invention is a stable concentrate, and a method of preparing it and using it, which contains a silver compound, an inorganic acid and an organic stabilizer. The concentrate is designed to be admixed with hydrogen peroxide to form a disinfectant.

Suitable silver compounds include silver nitrate ($AgNO_3$), silver sulfate ($Ag_2SO_4$), silver chloride (AgCl), and the sodium/silver chloride complex having the formula $AgNaCl_2$. Additional suitable silver compounds are silver benzoate ($C_6H_5-CO_2Ag$), silver carbonate ($Ag_2CO_3$), silver flouride (AgF), silver [I] oxide ($Ag_2O$) and silver [II]oxide (AgO). One or more silver compound(s) is/are added in such amounts that the concentrate contains 100 g$\pm$5% silver per liter of concentrate.

Colloidal silver compounds may also be used, in one-tenth of the concentration of grams Ag per liter of concentrate as described above. A suitable colloidal silver compound, available from Degussa AG, Zurich, contains 12 g per liter of silver in an aqueous solution of 5% by weight polyhydroxyl monocarboxylic acid.

Tartaric acid and/or citric acid are suitable stabilizers for use in combination with the silver compound(s). These acids should be added in the amount of approximately 50 g of one and/or the other per liter of concentrate.

Additional suitable organic acid stabilizers, to be used in stoichiometric amounts equivalent to amounts specified for incorporation of the tartaric and/or citric acids, include acetamidoacrylic acid ($H_2C=C(NHCOCH_3)CO_2H$), acetamidohexanic acid ($CH_3CONH(CH_2)_5CO_2H$), acetylbutyric acid ($CH_3CO(CH_2)_3CO_2H$), acrylic acid ($H_2C=CHCO_2H$), adipic acid ($HO_2C(CH_2)_4CO_2H$), maleic acid ($HO_2CCH_2CH(OH)CO_2H$), ethoxyacetic acid ($C_2H_5OCH_2CO_2H$), formic acid ($HCO_2H$), succinic acid ($HO_2CCH_2CH_2CO_2H$), butyric acid ($CH_3CH_2CH_2CO_2H$), hexanoic acid ($CH_3(CH_2)_4CO_2H$), hippuric acid ($C_6H_5CONHCH_2CO_2H$), malonic acid ($HO_2CCH_2CO_2H$), methanesulfonic acid ($CH_3SO_3H$), lactic acid ($CH_3CH(OH)CO_2H$), caprylic acid ($CH_3(CH_2)_6CO_2H$), oleic acid $CH_3(CH_2)_7$. $CH=CH(CH_2)_7CO_2H$, oxalic acid ($HO_2CCO_2H$), salicylic acid ($HOC_6H_4CO_2H$), and valeric acid $CH_3(CH_2)_3CO_2H$. Although each of the above organic acids is suitable for use with either the silver salt or the colloidal silver preparation, they are especially well suited for use with the various silver salts. Most preferred for use with the silver salt compounds are, however, the tartaric and/or citric acids.

Although each of the organic acid stabilizers listed above is suitable for use in combination with colloidal silver, the following are preferred for use, in amounts of approximately 100 g per liter of concentrate: acetonedicarboxylic acid ($HO_2CCH_2COCH_2CO_2H$), acetoxybenzoic acid ($CH_3CO_2C_6H_4CO_2H$), ethoxybenzoic acid ($C_2H_5OC_6H_4CO_2H$), ethylbenzoic acid ($C_2H_5C_6H_4CO_2H$), aminobenzoic acid ($H_2NC_6H_4CO_2H$), benzoic acid ($C_6H_5CO_2H$), bromobenzoic acid ($BrC_6H_4CO_2H$), bromosalicylic acid ($BrC_6H_3$-2-$(OH)CO_2H$), fluorosulfonyl-benzoic acid ($FSO_2C_6H_4CO_2H$), hydroxybenzoic acid ($HOC_6H_4CO_2H$), and phthalic acid ($C_6H_4$-1,2-$(CO_2H)_2$). Although they are preferred for use with colloidal silver, with the various benzoic acid stabilizers being most preferred, these organic acid stabilizers may also be used with the silver salts identified above.

An inorganic acid is used to reduce the pH of the silver- and stabilizer-containing composition. In general, 75% aqueous phosphoric acid, 65% aqueous nitric acid or 69% aqueous sulphuric acid is used. Hydrobromic acid Hydrochloric acid or boric acid are likewise suitable. It is recommended that the same acid be used as will later be used to stabilize the commercial hydrogen peroxide, which will be mixed with the concentrate. The acid serves as a pH regulator, but also acts as an additional stabilizer for the silver compound and for the ready-to-use product. For this reason, it is necessary to add acid in excess of the amount required to adjust pH. The entire amount of acid in the finished concentrate is at least equimolar to the existing amount of silver, preferably in excess, for example, of about 100 g of aqueous acid per liter of concentrate.

If the concentrate, after it is mixed with hydrogen peroxide to become a ready-to-use disinfectant, will be exposed for a long time to UV-radiation, for example solar radiation, etc., as in the case of an open-air swimming pool, it is advisable to add gelatin to the concentrate at at least 20° C. before homogenization; in general, this addition amounts to about 20 g per liter of concentrate and protects the silver against the effects of UV-radiation.

It is advantageous to manufacture the concentrate at a minimum temperature of 20° C. and under red light until bottling is completed, for example, in containers of colored glass or plastic without pigment.

The concentrate of the present invention is of unlimited durability, even at tropical temperatures, and remains, in contrast to well-known products, a clear, colorless, homogenous fluid (similar to water) which does not thicken after a long period of time. This lasting homogeneity of the product is a significant advantage because it permits optional future portioning of the concentrate without the renewed homogenizing that was necessary until the development of the present invention.

The concentrate may be mixed with hydrogen peroxide of 35 to 50% by weight (in water) at a volume ratio from 1:99 to 1:199. The resulting ready-to-use agent has an Ag concentration between 0.05 and 0.1% by weight. At a ratio of over 1:199, the product loses the silver/hydrogen peroxide synergy characteristics. At a ratio of less than 1:99, the possibility arises that the silver will precipitate from the admixture. The product within the above-mentioned limits has a shelf-life of at least 2 years.

The concentration of added hydrogen peroxide can, for certain applications, easily amount to 35% by weight, yet the product decomposes more quickly and the rate of disinfection is lower than that obtained by using 50% by weight hydrogen peroxide.

No renewed homogenizing of the concentrate before mixing it with hydrogen peroxide is necessary, due to the stable homogeneity of the concentrate.

Disinfectants of this type, mixed with hydrogen peroxide and ready to use, can then be bottled in customary transport and marketing containers, which should be equipped with a safety device to reduce any excessive gas pressure, for example a pressure relief valve. The chemical agents can last in such containers at a temperature between 4 and 25° C. for about 2 years without any danger. At higher temperatures, a longer period of storage is not recommended, since hydrogen peroxide tends to release gas.

The disinfectants invented are suitable for sterilizing water, foodstuffs and animal feeds, stationary surfaces, etc. The concentrate is added in very small amounts, in general amounting to about 10 to 75 ppm when added as a so-called "material disinfecting agent," to such things as bath water, drinking water, foodstuffs, cooking water, etc., or is used as a 0.1 to 2% by weight solution for surface disinfection. The products or objects disinfected with these new agents exhibit absolutely no change in smell, taste or appearance, are non-toxic, produce neither skin irritations nor other health impairments or injuries, and are completely inert with respect to ordinary materials such as concrete, wood, stone, glass, metals, porcelain, ceramic, plastics, textiles, etc.

The ready-to-use agent has a pH of about 2, and should be adjusted to this pH, if necessary, preferably by adding an additional quantity of the inorganic acid already present in the composition. In contrast to chlorine, the agent itself does not change the pH of the product to which it is added, primarily because only small amounts need be used. It can be used within broader temperature limits than chlorine, also, namely between 0 and 95° C., and the disinfecting effect increases with the rising temperature.

In the concentrations given above, the new agents are widely able to annihilate pathogenic germs. They fight, among other things, Gram-positive and Gram-negative bacteria, bacteriophage, viruses, etc., such as *E. coli, Proteus mirabilis, Staphylococcus aureus, Streptococcus faecalis, Pseudomonas aeruginosa, Mycobacterium tuberculosis, Candida albicans,* etc.

The new agents are especially suitable for sterilization: in the foodstuffs and animal feed industries, including the canning industry, for preservation of fresh products, for processing of fish for partial or complete preserving, and for disinfection in slaughterhouses; in the beverage industry, and in breweries, for the preparation of mineral water, in the production of wine and spirits, in production of fruit and vegetable juices, for disinfection of bottles and casks, and in water to be added to concentrates; in water disinfection for drinking water in wells or storage containers, in swimming pools, and in hot whirlpools; as well as in dairies, in farming, in the chemical and pharmaceutical industries, in laboratories and hospitals, for fighting diseases, etc.

In the following examples, all percentages are relative to weight, provided no other notations are given.

EXAMPLE I

At over 20° C. and under red light, 75% phosphoric acid was, slowly and by portions, added and stirred into 1 liter fully desalted water until the pH was equal to or less than 1.6. The mixture was stirred and heated to 55° C. and, with stirring, was mixed with 140 g silver nitrate. Stirring continued until complete homogenization occurred.

The solution was left to cool to about 25 to 30° C.; 75% phosphoric acid was then slowly stirred in by portions so that the entire quantity of aqueous phosphoric acid equalled 100 g in solution. The mixture was then, without stirring, allowed to reach room temperature (20°-25° C.), at which point 50 g tartaric acid was added.

The resulting mixture was next homogenized, in this particular case after addition of 20 g of gelatin, which was stirred in at a temperature which exceeded 20° C. A crystal-clear solution resulted. The same result has been reached when, in place of aqueous phosphoric acid, 65% nitric acid or 37% Hydrochloric acid or 69% sulphuric acid is added for a total addition of 100 g acid, and/or when the silver nitrate is replaced by 135 g silver sulfate or 124 g silver chloride or 176 g sodium/silver chloride complex ($AgNaCl_2$), and/or when, instead of tartaric acid, 50 g citric acid or 50 g of a mixture of citric acid and tartaric acid is used.

EXAMPLE II

To manufacture 11 liters of concentrate, 1 liter of distilled water was, slowly and by portions, mixed at about 55° C. with 850 g sodium or potassium benzoate. Stirring was then stopped, and the mixture was kept at 55° C.

In a separate container, 8350 g of colloidal silver solution (12 g per liter Ag in 5% hydrous polyhydroxyl monocarboxylic acid solution from Degussa AG) were added slowly and by portions to 75% phosphoric acid, 65% nitric acid or 69% sulphuric acid to yield a pH less than or equal to 1.6, and the mixture was warmed to 55° C.

To this mixture 1100 g of the aqueous sodium or potassium benzoate prepared above were then added, and the mixture was homogenized well. It was subsequently allowed to cool, without stirring, at room temperature (20°-25° C.). To the cooled mixture was then added, by stirring, an amount of the same inorganic acid to adjust pH such that the entire amount equalled 800 g; the addition was made slowly and by stirring in portions. This caused the mixture to homogenize well. Through addition of 200 g of gelatin at a minimum of 20° C. and renewed homogenizing, a concentrate was obtained which was well suited for disinfecting swimming pools; ultraviolet radiation did not affect the composition during use.

EXAMPLE III

Five liters of concentrate, obtained according to Example I, were mixed at volume ratio 1:99 with 50% by volume $H_2O_2$, at room temperature, under red light, and in a retort made of stainless steel, until homogenized. After formation of bubbles ceased, the product was bottled. This product was especially suitable for long-term disinfection, particularly at high temperatures, such as an additive for hot whirlpools, recycled water for water-cleaning installations, etc., preferably in a concentration from 40 to 75 ppm.

EXAMPLE IV

Eleven liters of concentrate, obtained according to Example II, were processed at a ratio of 1:19.9, as in Example III, with 50% by volume $H_2O_2$ into a finished product. The resulting product is suitable, for example, for disinfection of drinking water in a concentration from 10 to 34 ppm, for the surface disinfection in a 0.1 to 2% solution.

Although the invention has been described with reference to specific methods and materials, the invention is to be limited only insofar as is set forth in the accompanying claims.

I claim:

1. A process for preparing a storage stable, clear concentrate of unlimited durability which, upon admixture with hydrogen peroxide, forms a disinfectant, comprising:
    (a) admixing an inorganic acid with water, said water being selected from the group consisting of distilled water and fully desalted water, to yield aqueous inorganic acid having a pH less than or equal to 1.6;
    (b) admixing said aqueous acid at a temperature between 50 and 60° C. with a silver composition, selected from the group consisting of silver salts and silver salt complexes, in an amount which yields 95-105 g Ag per liter of the final concentrate;
    (c) cooling the resultant admixture to between 25 and 30° C., and adding such an amount of the same acid as was used for adjusting the pH of the water whereby the total amount of said acid is at least equimolar with the amount of silver present;
    (d) adding to said admixture an organic acid stabilizer, and optional gelatin, at 20 to 25° C.; and
    (e) homogenizing the obtained mixture.

2. The process according to claim 1 wherein the inorganic acid is selected from the group consisting of phosphoric acid, nitric acid and sulfuric acid, preferably in an amount of 100 g per liter water.

3. The process according to claim 1 wherein the silver compound added in step (b) is selected from the group consisting of silver nitrate, silver sulfate, silver chloride, sodium/silver chloride complex, silver benzoate, silver carbonate, silver fluoride, silver oxide and silver oxide, in an amount which yields approximately 95-105 g Ag per liter of the final concentrate; and the organic acid added in step (d) is selected from the group consisting of tartaric acid, citric acid and compositions containing both tartaric acid and citric acid, preferably in an amount of 100 g per liter water.

4. The process for the manufacture of a disinfectant, comprising admixing, at a temperature of at least 20° C. and optionally under red light, a concentrate, prepared in accordance with the process of one of claims 1, 2, or 3, with 35-50% by volume aqueous hydrogen peroxide at a ratio between 1:99 and 1:199 concentrate to aqueous hydrogen peroxide, whereby the ratio is chosen to yield a resultant composition having an Ag concentration between 0.05 and 0.1% by weight.

5. A process for preparing a storage stable, clear concentrate of unlimited durability which, upon admixture with hydrogen peroxide, forms a disinfectant, comprising:
    (a) admixing an inorganic acid with an aqueous solution containing colloidal silver solution in 5% aqueous polyhydroxymonocarboxylic acid, to yield a solution having a pH less than or equal to 1.6;
    (b) heating said aqueous solution to between 50 and 60° C. and adding thereto a solution of an organic stabilizer in distilled or fully desalted water having about the same temperature in an amount which yields approximately 9.5–10.5 g Ag per liter of the final concentrate;

(c) cooling the admixture to 20° to 25° C.;

(d) adding thereto such an amount of the same inorganic acid as was used for adjusting the pH that the total amount of inorganic acid is at least equimolar with the amount of silver present;

(e) optionally adding gelatin; and (f) homogenizing the admixture.

6. The process according to claim 5 wherein the colloidal silver is added in the form of an aqueous solution which further contains about 5% by weight of polyhydroxyl carboxylic acid, and wherein a benzoic acid stabilizer, and optional gelatin, are added.

7. The process according to any of claims 1, 5, 2, 3 or 6 wherein said inorganic acid is mixed with said water at a temperature of at least 20° C.

8. The product prepared in accordance with the process of any of claims 1, 5, 2, 3, or 6.

9. The process according to claim 5 wherein the inorganic acid is selected from the group consisting of phosphoric acid, nitric acid and sulfuric acid, preferably in an amount of 100 g per liter water.

10. The product prepared in accordance with the process of claim 7.

11. The process for the manufacture of a disinfectant, comprising admixing, at a temperature of at least 20° C. and optionally under red light, a concentrate, prepared in accordance with the process of one of claims 5, 6 or 7, with 35–50% by volume aqueous hydrogen peroxide at a ratio between 1:9.9 and 1:19.9 concentrate to aqueous hydrogen peroxide, whereby the ratio is chosen to yield a resultant composition having an Ag concentration between 0.05 and 0.1% by weight.

12. The disinfectant product obtained in accordance with the process of either of claims 4 or 11.

* * * * *